United States Patent
Wang et al.

(10) Patent No.: US 9,278,087 B2
(45) Date of Patent: Mar. 8, 2016

(54) DERIVATIVE OF BUTYLPHTHALIDE AND PREPARATION METHOD AND USE THEREOF

(71) Applicant: Shijiazhuang Yiling Pharmaceutical Co., Ltd, Shijiazhuang, Hebei (CN)

(72) Inventors: Wei Wang, Hebei (CN); Yayao Zhou, Hebei (CN); Ya'nan Liu, Hebei (CN)

(73) Assignee: Shijiazhuang Yiling Pharmaceutical Co., Ltd., Hebei (CN)

( * ) Notice: Subject to any disclaimer, the term of this patent is extended or adjusted under 35 U.S.C. 154(b) by 0 days.

(21) Appl. No.: 14/351,424

(22) PCT Filed: Sep. 26, 2012

(86) PCT No.: PCT/CN2012/081963
§ 371 (c)(1),
(2) Date: Apr. 11, 2014

(87) PCT Pub. No.: WO2013/053287
PCT Pub. Date: Apr. 18, 2013

(65) Prior Publication Data
US 2014/0288027 A1    Sep. 25, 2014

(30) Foreign Application Priority Data
Oct. 13, 2011   (CN) .......................... 2011 1 0309074

(51) Int. Cl.
| | |
|---|---|
| *C07D 307/88* | (2006.01) |
| *C07F 9/655* | (2006.01) |
| *A61K 31/365* | (2006.01) |
| *A61K 31/665* | (2006.01) |
| *A61K 47/26* | (2006.01) |
| *A61K 9/00* | (2006.01) |
| *A61K 9/48* | (2006.01) |

(52) U.S. Cl.
CPC .............. *A61K 31/365* (2013.01); *A61K 9/0019* (2013.01); *A61K 9/4858* (2013.01); *A61K 31/665* (2013.01); *A61K 47/26* (2013.01); *C07D 307/88* (2013.01); *C07F 9/65517* (2013.01)

(58) Field of Classification Search
CPC  C07D 307/88; C07F 9/65517; A61K 31/365; A61K 31/665; A61K 47/26
See application file for complete search history.

(56) References Cited

FOREIGN PATENT DOCUMENTS

| | | | |
|---|---|---|---|
| CN | 1257706 | | 6/2000 |
| CN | 101289438 | * | 10/2008 |
| CN | 101289438 | | 4/2012 |
| CN | 102503919 | | 6/2012 |
| EP | 1679070 | | 7/2006 |
| WO | 2005102314 | | 3/2005 |
| WO | WO 2005/102314 | * | 3/2005 ............. A61K 31/34 |

OTHER PUBLICATIONS

International Search Report issued in International Application No. PCT/CN2012/081963 mailed on Jan. 3, 2013.

* cited by examiner

*Primary Examiner* — Erich A Leeser
(74) *Attorney, Agent, or Firm* — Greenberg Traurig, LLP; David J. Dykeman; Fang Xie

(57) ABSTRACT

(−)-(S)-3-(3'-hydroxy)-butylphthalide (a compound shown by Formula I) and an ester formed of the same and an acid are proved by experiments to be applicable to treatment and prevention of cerebral ischemic diseases and have a sleep-improving function. The acid refers to a pharmaceutically acceptable inorganic or organic acid. The inorganic acid refers to nitric acid, sulfuric acid, or phosphoric acid. In addition to an acid radical, the organic acid at least comprises at least one of an amino group, a hydroxyl group, and a carboxyl group. None of the compound shown by Formula I and the ester thereof is water-soluble. An ester generated from the compound and the acid further react with an acid or a base to generate a salt which is water-soluble and is used to prepare injection preparation. The experiment proves that the salt does not stimulate vessels.

(I)

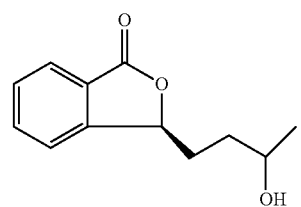

4 Claims, No Drawings

DERIVATIVE OF BUTYLPHTHALIDE AND PREPARATION METHOD AND USE THEREOF

CROSS-REFERENCE TO RELATED APPLICATIONS

This application is a national phase filing under 35 U.S.C. 371 of International Application No. PCT/CN2012/081963 filed on Sep. 26, 2012, which claims the benefit of and priority to Chinese Patent Application No. 201110309074.X filed Oct. 13, 2011, both of which applications are hereby incorporated by reference in their entirety.

FIELD OF THE INVENTION

The present invention belongs to the medical field of a compound, relates to (−)-(S)-3-(3'-hydroxy)-butylphthalide and an ester formed of the same with an acid, and discloses the preparation method and use thereof.

BACKGROUND OF THE INVENTION

Butylphthalide has improving effects on impairment of central nervous system function in patients with acute ischemic stroke, can promote the recovery of function in patients, and is mainly converted in vivo into two metabolites, 3-3-(3'-hydroxy)butylphthalide and 3-hydroxy-3-butylphthalide:

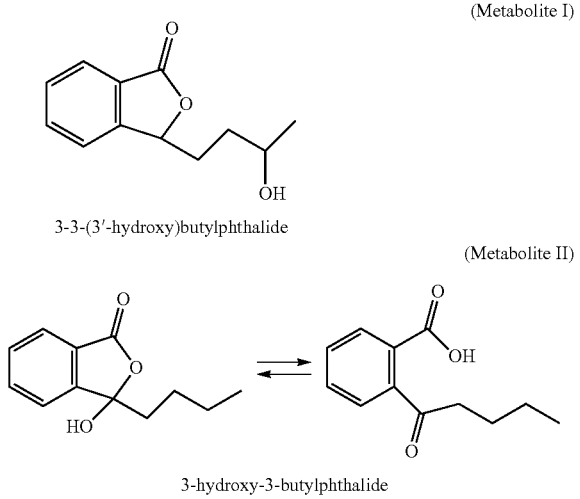

3-3-(3'-hydroxy)butylphthalide (Metabolite I)

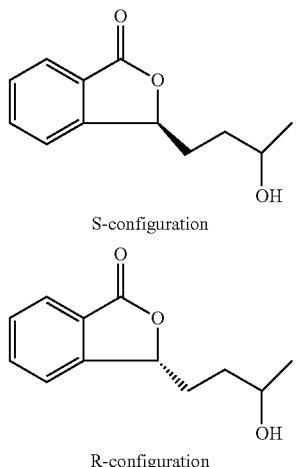

3-hydroxy-3-butylphthalide (Metabolite II)

Guangdong Zhongke Drug Research & Development Co. Ltd. and Shandong Lvye Natural Drug Research & Development Co. Ltd. synthesized a succinic acid ester, a glycine ester and a phosphoric acid ester of the Metabolite I, and illustrated the use thereof for preventing cerebral ischemic diseases in 2008. Patent application 200410036628.3 discloses a novel use of butylphthalide homologs 3-(3'-hydroxy)butylphthalide and 3-hydroxy-3-butylphthalide. Both of them are proved to have the following effects:

1) significantly improving neurologic symptoms in rats caused by cerebral ischemia due to brain trauma;

2) improving memory disorder in rats caused by cerebral ischemia;

3) relieving cerebral edema in rats caused by cerebral ischemia;

4) reducing stroke in rats caused by cerebral ischemia;

5) improving energy metabolism in rats caused by cerebral ischemia;

6) increasing cerebral blood flow in the ischemic brain region;

7) reducing the area of cerebral infarction in rats with local cerebral ischemia and relieving symptoms of neurological deficit;

8) anti-platelet aggregation and anti-thrombosis;

9) preventing and treating dementia.

Researchers in our company discover that the Metabolite I has two different optical isomers, and have prepared the compound of 3-3-(3'-hydroxy)butylphthalide (Metabolite I) in both S- and R-configurations as is shown in the following figures, by a method of asymmetric synthesis:

Furthermore, it is found by animal tests that the R-configuration cannot affect the cerebral infarct volume in rats with cerebral ischemia and improve the symptoms of cerebral ischemia, while the S-configuration has effects of improving the symptoms of cerebral ischemia and decreasing the cerebral infarct volume in rats with cerebral ischemia. It is also found that the S-configuration of the Metabolite I (the compound of claim 1) has the effect of improving sleep.

The S-configuration of the Metabolite I (the compound of claim 1) is an oily liquid and is insoluble in water. Therefore, in order to prepare it into a dosage form of injectable solution, we have conducted further studies to allow it to become a water-soluble compound by forming an ester with an acid and then forming a salt, to meet the requirement of the formulation.

SUMMARY OF THE INVENTION

The purpose of the present invention is to provide a derivative of 3-(3'-hydroxy)butylphthalide for ischemic stroke, and the preparation method and use thereof.

To achieve the purpose mentioned above, the present invention employs the following technical solutions.

Preparing the compound of formula 1 as shown in the following figure,

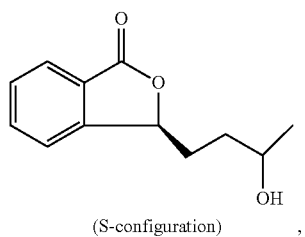

(S-configuration), formula I and preparing the compound in R-configuration as shown in the following figure,

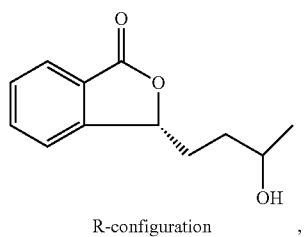

R-configuration, by asymmetric synthesis.

It is proved by animal tests that the compound in R-configuration does not have the effect of reducing the cerebral infarct volume of cerebral ischemia in rats, cannot improve the symptoms of cerebral ischemia, and does not have the effect of improving sleep, while the S-configuration has very good effects of improving the symptoms of cerebral ischemia, and can improve the sleeping state in animals.

The compound of formula 1 is an oily substance insoluble in water. Therefore we allow it to form an ester with an acid, wherein the acid refers to a pharmaceutically acceptable inorganic or organic acid. The inorganic acid refers to nitric acid, sulfuric acid or phosphorus acid. The organic acid further contains one type of group, and at least one group selected from amino, hydroxy or carboxyl group in addition to acid radical. The salt from an ester is soluble in water and can be prepared into the dosage form of an injectable solution or lyophilized powder injection.

The organic acid can be amino acids, specifically refer to glycine, alanine, lysine, arginine, serine, phenylalanine, proline, tyrosine, aspartic acid, glutamic acid, histidine, leucine, methionine, threonine, pyroglutamic acid, tryptophan or valine.

Wherein, an ester formed with glycine is preferred, which is as shown in the following figure:

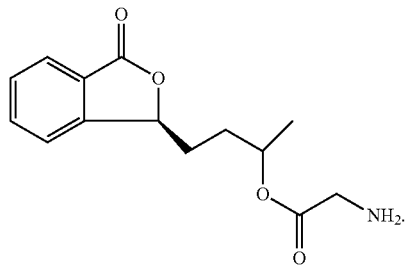 [SMILES: CC(CC[C@@H]1OC(=O)c2ccccc21)OC(=O)CN]

The organic acid can also be a dicarboxylic acid, specifically camphoric acid, malic acid, citric acid, maleic acid, succinic acid, oxalic acid, glutaric acid, ethanedioic acid or malonic acid.

Wherein, an ester formed with succinic acid is preferred, which is as shown in the following figure:

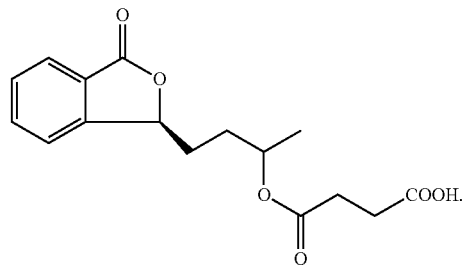 [SMILES: CC(CC[C@@H]1OC(=O)c2ccccc21)OC(=O)CCC(=O)O]

The organic acid can also refer to pamoic acid, hydroxynaphthoic acid, gentisic acid, salicylic acid, hydroxyacetic acid, mandelic acid, lactic acid, 4-acetamidobenzoic acid or nicotinic acid.

The compound of formula I forms an ester with an inorganic acid, preferably phosphoric acid, which is as shown in the following figure:

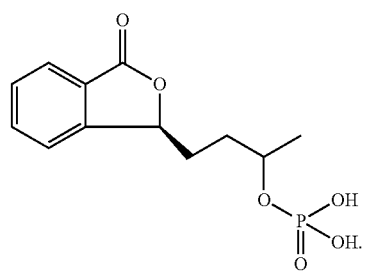 [SMILES: CC(CC[C@@H]1OC(=O)c2ccccc21)OP(=O)(O)O]

The above ester further forms a salt, so as to be prepared into a water-soluble compound to solve the problem of water-solubility, and thus can be used to prepare an injectable dosage form.

An ester formed by the compound of formula I with glycine preferably forms a hydrochloride, which is as shown in the following figure:

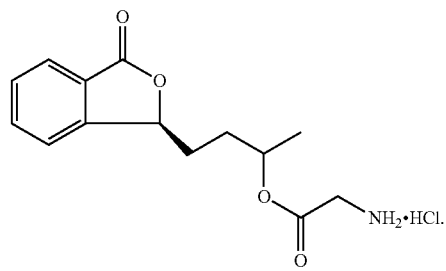

The present invention further provides a salt of the dibasic acid esters of the compound of formula I, which refers to a salt formed with potassium, sodium, magnesium or organic amine. The organic amine radical can be tromethamine, diethanolamine, triethanolamine, glycine, lysine or arginine.

Wherein, the sodium salt is preferred, which is shown in the following figure:

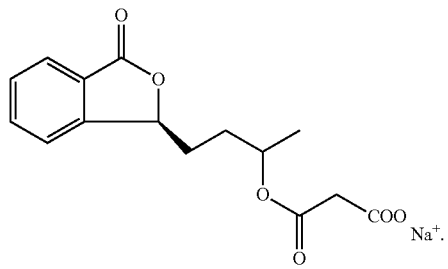

In order to solve the problem of water-solubility, the ester formed by the compound of formula I with phosphoric acid can further form a salt with physiologically acceptable base, which refers to sodium salt, potassium salt, magnesium salt or organic amine salt. The organic amine includes lysine, glycine, arginine, tromethamine, diethanolamine or triethanolamine.

The ester formed by the compound of formula I with phosphoric acid preferably forms a disodium salt, which has the following structural formula:

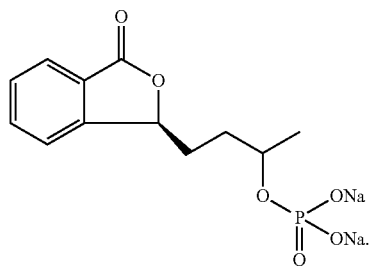

The present invention further provides a pharmaceutical composition for treating ischemic stroke, characterized in that the composition comprises a therapeutic effective amount of the compound of general formula (1) or a salt thereof and a pharmaceutical acceptable carrier. The pharmaceutical composition can be an oral formulation or an injectable formulation.

Experiments for muscular and vascular irritations indicate that, it is administered by injection after the ester formed by the compound of formula I with an acid further forming a salt. No muscular and vascular irritations are observed, so that it can be used as injectable formulation.

DETAILED EMBODIMENTS

Example 1

Preparation of Various Compounds

The compounds herein have very strong continuity. Therefore, in order to describe the preparation method of various compounds in a detailed, accurate and convenient way, the method is illustrated by way of one example. In the following synthetic route, each compound is indicated by a serial number. For a more concise illustration, in the preparation method below, the compounds are replaced by the serial numbers.

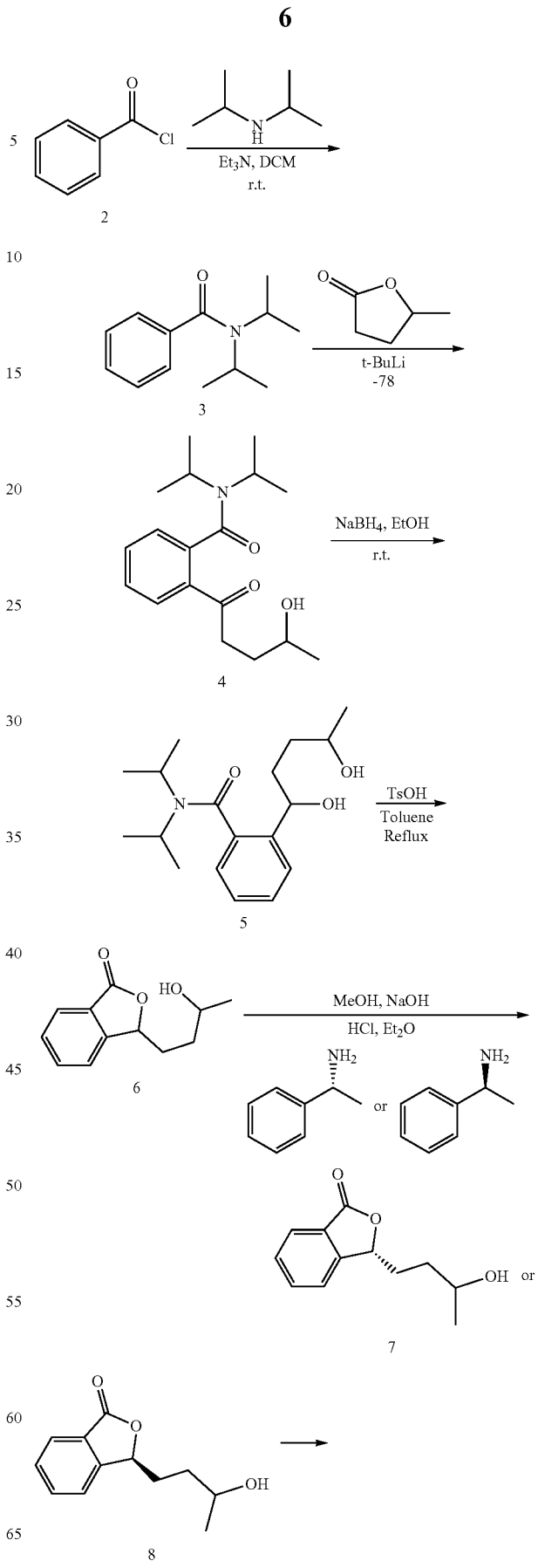

-continued

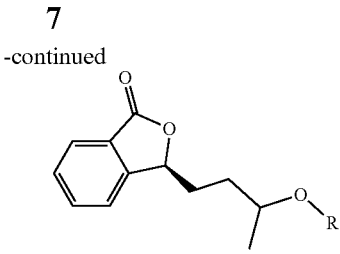

1a-c

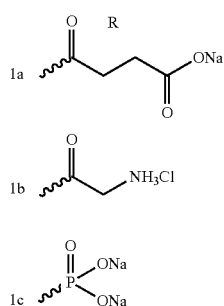

When the R in the above scheme is different groups, different compounds 1a, 1b and 1c are obtained.

(1). Synthesis of Compound 3:

Diisopropylamine (1.3 mol) was placed into a 2000 mL round bottom flask, and 1000 mL anhydrous dichloromethane was added. After dissolving, triethylamine (2.0 mol) was added, and Compound 2 (1.0 mol) was added dropwise in an ice bath. After completing the dropwise addition, the reaction mixture was warmed to room temperature, and stirred overnight. 500 mL Dichloromethane was added to dilute, and the reaction mixture was washed respectively with 5% dilute hydrochloric acid (500 mL×1), water (500 mL×1) and brine (500 mL×1), dried over anhydrous sodium sulfate, and concentrated, to obtain 202.4 g Compound 3. The crude yield was 99%, MS (m/z): 206.1.

(2). Synthesis of Compound 4:

Compound 3 (0.8 mol) was dissolved in 500 mL dry tetrahydrofuran, and tert-butyllithium (1.0 mol) was gradually added dropwise at −78° C. After the completion of the dropwise addition, tetramethylethylenediamine (1.2 mol) was added, and stirred at −78° C. for 30 min. Lactone (1.0 mol) was added dropwise into the above mixture, gradually warmed to room temperature, and continued to react for 5 hr. The reaction was quenched by adding saturated ammonium chloride solution, and the organic solvent was removed by reduced pressure distillation. The residue was extracted by ethyl acetate, concentrated under reduced pressure, and recrystallized, to obtain 222.4 g Compound 4. The yield was 91%.

HNMR (400 Hz, CDCl$_3$): 8.08-8.06 (m, 1H), 8.04-8.02 (m, 1H), 7.63-7.61 (m, 1H), 7.60-7.58 (m, 1H), 3.95-3.93 (m, 2H), 3.40-3.38 (m, 1H), 2.55 (t, J=1.2 Hz, 2H), 1.64-1.62 (m, 2H), 1.25 (d, J=1.5 Hz, 12H), 1.21 (d, J=1.6 Hz, 3H); MS (m/z): 306.2.

(3). Synthesis of Compound 5:

220 g Compound 4 (0.7 mol) was dissolved in 500 mL methanol, sodium borohydride (1.40 mol) was added in small batches in an ice bath, and stirred overnight at room temperature under the protection of nitrogen gas. After the completion of reaction, about 20 mL concentrated hydrochloric acid was added dropwise to decompose the excess sodium borohydride. Methanol was removed by reduced pressure distillation. The residue was extracted by dichloromethane, washed with water, washed with brine, dried over anhydrous sodium sulfate, concentrated, and recrystallized, to obtain 204.8 g Compound 5. The yield was 95%. MS (m/z): 308.2.

(4). Synthesis of Compound 6:

Compound 5 (0.60 mol) was dissolved in 500 mL toluene, catalytic amount of p-toluenesulfonic acid (about 1%) was added, and boiled slightly and refluxed under the protection of nitrogen gas for 8 days. Toluene was removed by reduced pressure distillation, dichloromethane was added to dilute, and the residue was washed with water, washed with brine, dried over anhydrous magnesium sulfate, and passed through a column, to obtain 106.4 g Compound 6. The yield was 86%. MS (m/z): 207.2.

(5). Synthesis of Compound 7:

Compound 6 (0.2 mol) was dissolved in 200 mL methanol, sodium hydroxide aqueous solution (16 g/40 mL) was added under stirring, and completed over 15 min. The system was heated to become a homogenous solution, and continued to react at room temperature for 2 hr. The reaction was quenched, and methanol was removed by reduced pressure distillation. An appropriate amount of distilled water was added into the residual solution to dilute. The system was cooled to −5° C. or below, and adjusted to pH=3~4 with 5% hydrochloric acid solution, and extracted with diethyl ether (100×3). The diethyl ether extracts were pooled, and the solution was cooled to −5° C. or below. 0.2 mol (+)-(R)-α-Phenylethylamine was slowly added dropwise. The system was maintained at a temperature of −5° C. or below, and allowed to stand for 3 hr. Plenty of crystals were precipitated, and the system was filtered to collect the crystals. The crystals were recrystallized twice with acetone or ethyl acetate to obtain 20.3 g crystals, and the concentration of the crystals was 15 g crystals/100 mL solvent. The crystals were dissolved in 10 volumes of distilled water, and sodium hydroxide was added to adjust the solution to pH=13. (+)-(R)-α-Phenylethylamine was recovered by extraction with diethyl ether, and the aqueous phase was adjusted to pH=2 with hydrochloric acid, extracted with diethyl ether, dried, and concentrated, to obtain a crude product of (+)-(R)-3-(3'-hydroxy)butylphthalide. The crude product was recrystallized with ethanol to obtain 8.7 g Compound 7. The yield was 21%. [α]$_D$=+66.80 (c=1.02, CH$_3$OH).

HNMR (400 Hz, CDCl$_3$): 7.91-7.89 (m, 1H), 7.41-7.39 (m, 1H), 7.33-7.31 (m, 1H), 7.30-7.28 (m, 1H), 5.24 (t, J=1.2 Hz, 1H), 3.40-3.38 (m, 1H), 2.55 (t, J=1.2 Hz, 2H), 2.05-2.03 (m, 2H), 1.45-1.43 (m, 2H), 1.21 (d, J=1.6 Hz, 3H); MS (m/z): 207.2.

(6). Synthesis of Compound 8:

Compound 6 (0.2 mol) was dissolved in 200 mL methanol, sodium hydroxide aqueous solution (16 g/40 mL) was added under stirring, and completed over 15 min. The system was heated to become a homogenous solution, and continued to react at room temperature for 2 hr. The reaction was quenched, and methanol was removed by reduced pressure distillation. An appropriate amount of distilled water was added into the residual solution to dilute. The system was cooled to −5° C. or below, and adjusted to pH=3~4 with 5% hydrochloric acid solution under stirring, and extracted with diethyl ether (100×3). The diethyl ether extracts were pooled, and the solution was cooled to −5° C. or below. 0.2 mol (S)-α-phenylethylamine was slowly added dropwise. The system was maintained at a temperature of −5° C. or below, and allowed to stand for 3 hr. Plenty of crystals were precipitated, and the system was filtered to collect the crystals. The crystals were recrystallized twice with acetone or ethyl acetate to obtain 20.3 g crystals, and the concentration of the crystals was 15 g crystals/100 mL solvent. The crystals were dissolved in 10 volumes of distilled water, and sodium hydroxide was added to adjust the solution to pH=13. (S)-α-phenylethylamine was recovered by extraction with diethyl ether, and the aqueous phase was adjusted to pH=2 with hydrochloric acid, extracted with diethyl ether, dried, and concentrated, to obtain a crude product of (S)-3-(3'-hydroxy) butylphthalide. The crude product was recrystallized to obtain 8.7 g Compound 7. The yield was 21%. $[\alpha]_D = -66.80$ (c=1.02, $CH_3OH$).

HNMR (400 Hz, $CDCl_3$): 7.91-7.89 (m, 1H), 7.41-7.39 (m, 1H), 7.33-7.31 (m, 1H), 7.30-7.28 (m, 1H), 5.24 (t, J=1.2 Hz, 1H), 3.40-3.38 (m, 1H), 2.55 (t, J=1.2 Hz, 2H), 2.05-2.03 (m, 2H), 1.45-1.43 (m, 2H), 1.21 (d, J=1.6 Hz, 3H); MS (m/z): 207.2.

(7). Synthesis of Compound 1a:

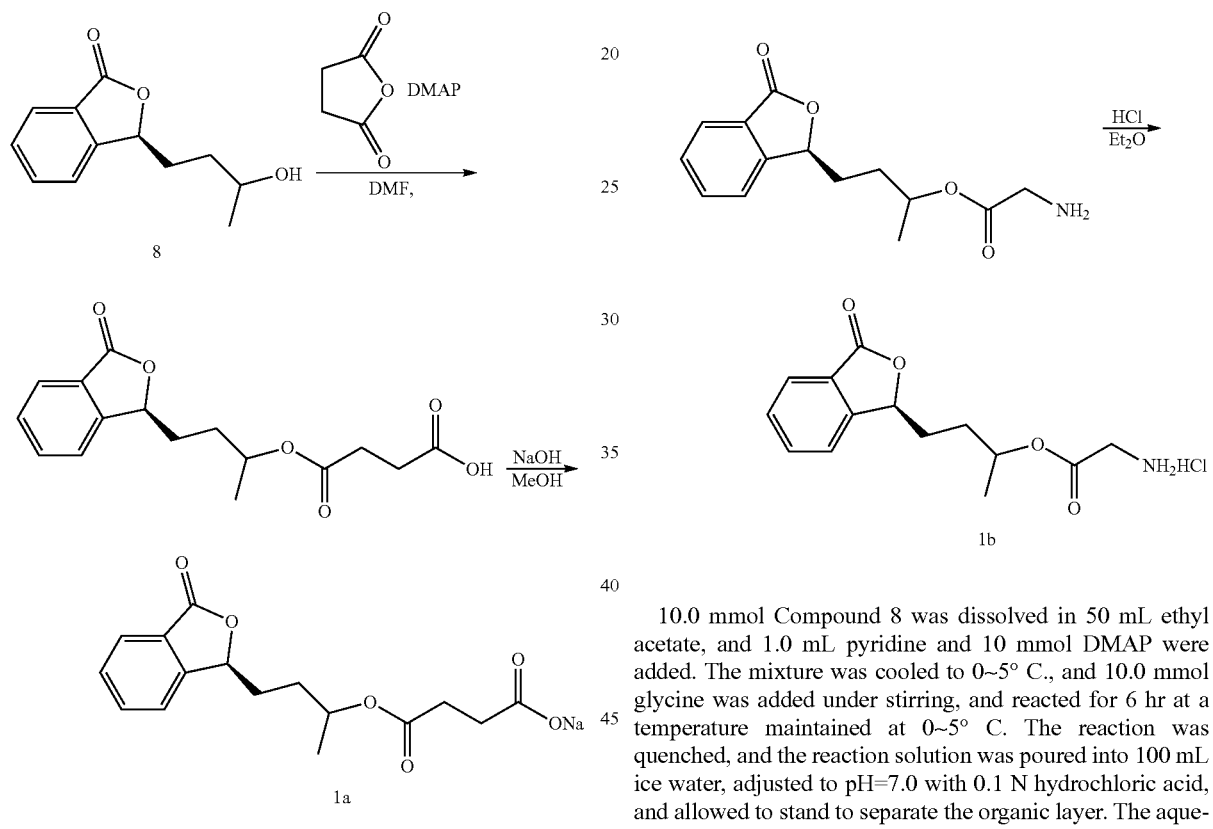

10.0 mmol Compound 8, 10.0 mmol butanedioic anhydride, and 10 mmol DMAP were dissolved in 50 mL DMF, heated to 85° C., and reacted for 6 hr. The reaction was quenched, and the 00 was poured into 200 mL ice water, adjusted to pH=2~3 with 0.1 N hydrochloric acid, and extracted with ethyl acetate (100 mL×3). The organic phase was pooled, washed with brine for three times, dried over anhydrous sodium sulfate, distilled under reduced pressure, to obtain (S)-3-(3'-succinate ester)butylphthalide, which was recrystallized to obtain 2.8 g white solid powders. The yield was 91%.

HNMR (400 Hz, $CDCl_3$): 7.8-7.78 (m, 1H), 7.65-7.63 (m, 1H), 7.49-7.47 (m, 1H), 7.44-7.42 (m, 1H), 5.50-5.46 (m, 1H), 3.82-3.74 (m, 1H), 2.72-2.66 (m, 2H), 2.62-2.56 (m, 2H), 2.05-2.03 (m, 2H), 1.45-1.43 (m, 2H), 1.21 (d, J=1.6 Hz, 3H); MS (m/z): 307.3.

The above (S)-3-(3'-succinate ester)butylphthalide was dissolved in 50 mL methanol and 4 mL 10% sodium hydroxide solution, heated to reflux for 2 hr, and concentrated to obtain a sodium salt of (S)-3-(3'-succinate ester)butylphthalide (Compound 1a), MS (m/z): 305.3.

(8). Synthesis of Compound 1b:

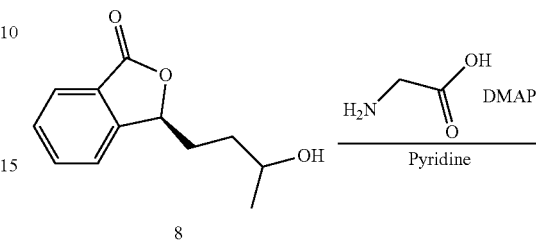

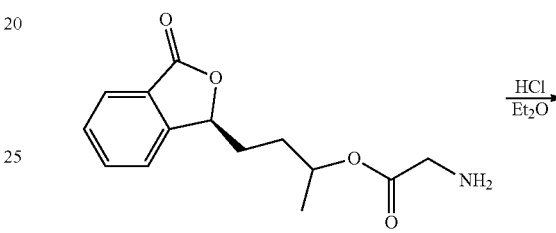

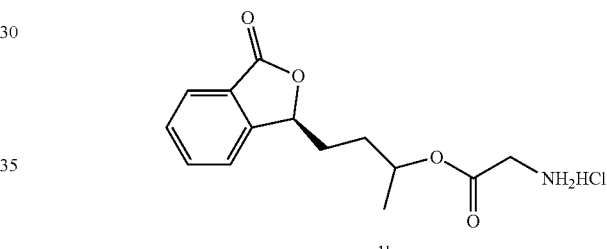

10.0 mmol Compound 8 was dissolved in 50 mL ethyl acetate, and 1.0 mL pyridine and 10 mmol DMAP were added. The mixture was cooled to 0~5° C., and 10.0 mmol glycine was added under stirring, and reacted for 6 hr at a temperature maintained at 0~5° C. The reaction was quenched, and the reaction solution was poured into 100 mL ice water, adjusted to pH=7.0 with 0.1 N hydrochloric acid, and allowed to stand to separate the organic layer. The aqueous phase was extracted with ethyl acetate (50 mL×3). The organic phase was pooled, and washed with brine for 3 times, dried over anhydrous sodium sulfate, distilled under reduced pressure to obtain (S)-3-(3'-glycinate ester)butylphthalide, which was recrystallized from ethanol to obtain 2.3 g white solid powder. The yield was 87%.

HNMR (400 Hz, $CDCl_3$): 7.8-7.78 (m, 1H), 7.65-7.63 (m, 1H), 7.49-7.47 (m, 1H), 7.44-7.42 (m, 1H), 5.50-5.46 (m, 1H), 3.82-3.74 (m, 1H), 3.62 (s, 2H), 2.05-2.03 (m, 2H), 1.45-1.43 (m, 2H), 1.21 (d, J=1.6 Hz, 3H); MS (m/z): 264.3.

The above (S)-3-(3'-glycinate ester)butylphthalide was dissolved in 50 mL acetone and 10 mL diethyl ether, and a diethyl ether solution of hydrochloride was added dropwise to adjust pH=2. Plenty of white solid was precipitated, filtered, dried to obtain 2.4 g (S)-3-(3'-glycinate ester)butylphthalide hydrochloride (Compound 1b). The yield was 80%. MS (m/z): 264.3.

(9). Synthesis of Compound 1c:

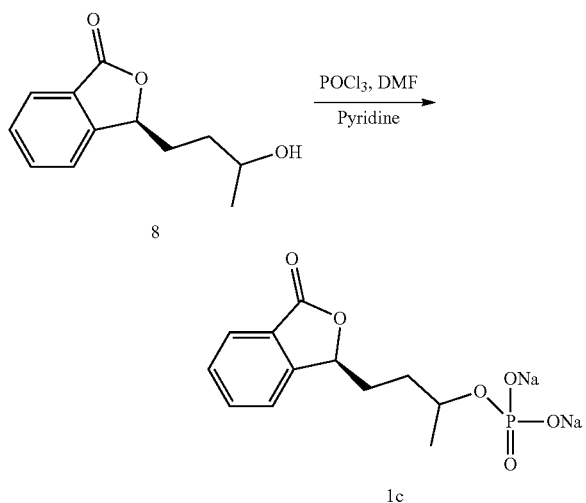

20.0 mL pyridine was added into 100 mL DMF, cooled to −10° C., and 25.0 mL phosphorus oxychloride was added under stirring. The mixture was stirred for 30 min, and then 10.0 mmol Compound 8 was added batchwise. After stirring for 3 hr, the reaction was quenched. The reaction solution was poured into 100 mL ice water, adjusted to pH=2 with 0.1 N hydrochloric acid, extracted with ethyl acetate (50 mL×3). The organic phase was pooled, washed with brine for 3 times, and dried over anhydrous sodium sulfate. The solvent was removed by reduced pressure distillation to obtain (S)-3-(3'-phosphate ester)butylphthalide. Then it was dissolved in 20 mL ethanol, and 10.6 sodium carbonate was added to react for 2 hr under a temperature of 30° C. The reaction was quenched, and 100 mL acetone was added. The mixture were allowed to stand and precipitated at 5° C., filtered, dried under vacuum, to obtain 2.8 g (S)-3-(3'-phosphate ester)butylphthalide disodium salt (Compound 1c), which was a while solid powder. The yield was 85%.

HNMR (400 Hz, CDCl$_3$): 7.91-7.89 (m, 1H), 7.41-7.39 (m, 1H), 7.33-7.31 (m, 1H), 7.30-7.28 (m, 1H), 5.24 (t, J=1.2 Hz, 1H), 3.40-3.38 (m, 1H), 2.05-2.03 (m, 2H), 1.65-1.63 (m, 2H), 1.21 (d, J=1.6 Hz, 3H); MS (m/z): 331.2.

Example 2

Preparation of injectable (−)-(S)-3-(3'-phosphate ester disodium)butylphthalide (Compound 1c in Example 1) lyophilized powder 10 g the prepared (S)-3-(3'-phosphate ester)butylphthalide sodium salt (Compound 1c) was taken, and 1000 ml water for injection was added to dissolve, and 60 g mannitol was further added. After dissolving completely, water for injection was additionally added to 1200 ml. After decarburization by activated charcoal, the mixture was filtered through microporous membrane, aliquoted into 7 ml penicillin bottle with 3 ml for each bottle, plugged, lyophilized, and glanded, to obtain the injectable lyophilized powder. Specification: 20 mg/bottle.

Example 3

Preparation of capsules of (S)-3-(3'-phosphate ester disodium)butylphthalide (Compound 1C)

| Formula: | (S)-3-(3'-phosphate ester)butylphthalide sodium salt | 60 g |
|---|---|---|
| | lactose | 105 g |
| | | 1000 capsules |

(S)-3-(3'-phosphate ester)butylphthalide sodium salt was accurately weighed according to the amount in the formula, sieved through 100 mesh screen, and lactose according to the formula amount, which was dried at 80° C. and sieved through 80 mesh screen, was added, mixed evenly. The mixture was detected for the contents, and filled into 1# capsule shells if qualified, to obtain the capsules.

Example 4

Preparation of injectable solution of (S)-3-(3'-phosphate ester disodium)butylphthalide (Compound 1c)

| Formula: | (S)-3-(3'-phosphate ester)butylphthalide sodium salt | 50 g |
|---|---|---|
| | water for injection | 4000 ml |
| | | 1000 ampoules |

(S)-3-(3'-phosphate ester)butylphthalide sodium salt (Compound 1c) was accurately weighed according to the amount in the formula, and an appropriate amount of water for injection was added. The pH was adjusted to 6.5-7.2, and water for injection was added to 4000 ml. 2 g activated charcoal for injection was added, boiled for 15 min, decarburized through filtering by suction. The solution was filtered through 0.22 μm microporous membrane, filled and sealed in glass ampoules, and autoclaved at 115° C. for 30 min, to obtain the injectable solution.

Example 5

Effects on Volumes of Cerebral Infarction in Rats with Local Cerebral Infarction (1) Experimental Materials and Method Wistar rats, body weight 250~280 g, were raised separately before and after the surgical operation, and kept at room temperature of 23~25° C. All the rats were allowed ad libitum access to food and water. tMCAO models were prepared according to the method of longa, et al. Rats were anaesthetized with 10% chloral hydrate (350 mg/kg, i.p.), and the body temperature was maintained at 37±0.5° C. The rat was fixed in supine position onto an operating table. The skin was cut along the midline of the neck, and the common carotid artery (CCA), external carotid artery (ECA) and internal carotid artery (ICA) on the right side were carefully isolated. The ECA was ligated and cut, and straightened in line with the ICA. A small incision was cut on the ECA, and a 4.0 cm long round-head silicified nylon thread with a diameter of 0.26 mm (coated with 0.1% polylysine) was inserted through this incision into the ICA for about 1.85~2.00 cm, until the starting place of the anterior cerebral artery of the rat, to block the blood supply of the middle cerebral artery. After 2 hr of ischemia, the nylon thread was pulled out carefully, the ECA incision was ligated, and the operational incision was sutured. The animal was returned to the cage for 24 hr reperfusion.

(2) Experimental Groups and Administration

Rats were randomly divided into 12 groups: model control group, water for injection (100 mg/kg), the administration group of the Compound 7 in Example 1 (25, 50, 100 mg/kg), the administration group of the Compound 8 in Example 1 (25, 50, 100 mg/kg), the administration group of DL-3-(3'-hydroxy)-butylphthalide (DL for short) (25, 50, 100 mg/kg). They were orally administered 10 min after the ischemia caused by MCA blockage.

(3) Determination of the Volume of Cerebral Infarction

After reperfusion injury in the rat for 24 hr, the rat was beheaded and the brain was taken out immediately. The olfactory tract, the cerebellum and the low brain stem were removed. The brain was coronally cut into 6 slices (the first slice to the fifth slice was 2 mm/slice, and the sixth slice was 4 mm), and they were rapidly placed into 5 ml solution containing 1.5 ml 4% TTC and 0.1 ml 1 M $K_2HPO_4$ to stain (37° C., shielded from light) for 20~30 min, wherein they are flipped once every 5 min. After the TTC staining, the normal tissue was dark stained and appeared red, and the infarcted tissue appeared white. Each group of brain slices were neatly arranged and were taken photos for preservation. The infarction area in each slice was calculated, and the infarction volume was finally converted by superposition. The infarction volume was expressed in percentage in a cerebral hemisphere, to eliminate the effects of cerebral edema.

Brain infarction volume(%)=(volume of the contralateral hemisphere to the operated side−volume of uninfarcted portion of the operated hemisphere)/volume of the contralateral hemisphere to the operated side*100%

(4) Experimental Results

After 2 hr of ischemia and 24 hr of reperfusion, the volume of cerebral infarction of the solvent control group was 33.8%. The sham operation group did not have any cerebral infarction. The results of the volume of cerebral infarction in other groups are as shown in Table 1.

TABLE 1

Effects of gavage administration on the volume of cerebral infarction in rats with local ischemia

| Sample | Volume of cerebral infarction (25 mg/kg group) | Volume of cerebral infarction (50 mg/kg group) | Volume of cerebral infarction (100 mg/kg group) |
|---|---|---|---|
| Compound 7 | 19.8% | 18.9% | 18.7.0% |
| Compound 8 | 14.6% | 13.8% | 11.8% |
| DL | 17.2% | 16.4% | 14.5% |
| Control group | | | 20.1% |

In comparison with the solvent control group, oral administration in groups of Compound 8 and DL-3-(3'-hydroxy)-butylphthalide can significantly reduce the volume of cerebral infarction, and groups of Compound 7 did not effectively reduce the volume of cerebral infarction. Groups of (−)-3-(3'-hydroxy)-butylphthalide (i.e. Compound 8) are superior to DL-3-(3'-hydroxy)-butylphthalide, indicating that Compound 8 in S configuration was the effective active ingredient, while Compound 7 in R configuration was not found to have the effect of reducing the volume of cerebral infarction caused by cerebral ischemia.

Example 12

Effects of Injection Administration of 1a, 1b, 1c on the Volume of Cerebral Infarction (1) Experimental Groups and Administration Rats of the ischemia blocking model in Example 11 were taken, and randomly divided into 12 groups: sham operation group, model control group, (water for injection, 10 mg/kg), 1a group (2.5 mg/kg, 5.0 mg/kg, 10 mg/kg), 1b group (2.5 mg/kg, 5.0 mg/kg, 10 mg/kg), and 1c group (2.5 mg/kg, 5.0 mg/kg, 10 mg/kg). 10 min after ischemia caused by MCA blockage, they were administered intravenously.

(2) Results and Discussion

The determination of the volume of cerebral infarction was the same to Example 4. After 2 hr of ischemia and 24 hr of reperfusion, the volume of cerebral infarction of the solvent control group was 33.6%. The sham operation group did not have any cerebral infarction. In comparison with the solvent control group, each of the groups can significantly reduce the volume of the cerebral infarction. In comparison with the solvent control group, all the groups of samples can significantly reduce the volume of the cerebral infarction, as is shown in Table 2.

TABLE 2

Effects of intravenous administration of the salt of MI ester on the volume of cerebral infarction in rats with local ischemia

| Sample | Volume of cerebral infarction (2.5 mg/kg group) | Volume of cerebral infarction (5.0 mg/kg group) | Volume of cerebral infarction (10.0 mg/kg group) |
|---|---|---|---|
| 1a | 21% | 15.4% | 11.8% |
| 1b | 21.3% | 16.0% | 12.0% |
| 1c | 20.6% | 15.8% | 11.7% |
| Control group | | | 33.6% |

Example 13

Experiments for Vascular Irritation of 1a, 1b and 1c

1) Design of Experiments 1a, 1b and 1c were taken and dissolved in water for injection, and were respectively prepared into two concentration groups. The high concentration group: 4.2 mg/ml, and the low concentration group: 1.4 mg/ml. They were administered intravenously through rabbit auricular veins, and the dosage was 5 ml.

2) Administration Method:

8 Healthy New Zealand rabbits were selected, and the test drug in high concentration and low concentration was respectively injected into the auricular vein of the left ear of the rabbits, while equal volume of an injectable solution of sodium chloride was injected into the auricular vein of the right ear of the rabbits. The 8 rabbits were administered successively with the test drug in high concentration and low concentration, and then administered respectively with 0.9% injectable solution of sodium chloride. This is conducted once every day for 3 consecutive days. The rabbits were weighed respectively before the administration, and 48 hr and 14 days after the administration.

3) General Observations and Sampling in Animals

The reactions of the animals and the injection site of the blood vessel were observed and recorded before the administration every day. 48 hr after the last administration, 2 New Zealand rabbits administered respectively with high concentration and low concentration were executed by bloodletting. The reactions of the blood vessel tissues were observed visually and recorded, then both ears of the rabbits were cut off from the roots of ear (firstly the left ear, then the right ear, and label them). Then, a section of specimen of the rabbit ear was cut out respectively, and fixed in 10% solution of neutral formaldehyde (the specimen was 8 cm long and 1 cm wide; the incision at the distal end to the heart was about 0.5 cm away from the first pinprick, and the incision at the proximal end to the heart was about 2 cm away from the third pinprick, and the proximal end to the heart was the end for hanging). 2 animals administered respectively with the test drug in high concentration and low concentration were left for further observation until the 14$^{th}$ day after the last administration, and pathological examination was conducted.

From the border of the first pinprick, one section was cut at the distal end; and from the border of the third pinprick, two sections were cut at the proximal end; the blood vessel was cut transversely when preparing the slices. The preparation of slices was conducted with conventional paraffin, and the thickness of the slice was 4~5 μm. H-E staining was conducted before performing histopathologic examination.

5) Result Judgment

Comprehensive judgment was conducted according to the visual observation and pathological examination. The reactions of the injection site of the animal blood vessel were visually observed and recorded before administration every day. During the administration, it was visually observed that the inner side and outer side of the vascular epidermis at the injection site of the rabbit ear in the administration side and the control side in some of the animals administered with the test drug in high concentration and low concentration appeared red, with an area from 0.1 cm×0.2 cm to 0.2 cm×1.0 cm. 48 hr after the last administration, the vascular profile of the blood vessel of the rabbit ear in both side of 4 rabbits administered with the test drug in high concentration and low concentration was clear, and the thickness of the rabbit ear was uniform, and no significant change was observed. 14 days after the last administration, necropsy was conducted in 4 rabbits administered with the test drug in high concentration and low concentration. The vascular profile of the rabbit ear in both sides was relatively clear, and the thickness of the rabbit ear was uniform, and no significant change was observed.

Necropsy in 4 rabbits administered with the test drugs in high concentration and low concentration was conducted 40 hr after the last administration, and the necropsy in the other 4 rabbits administered with the test drugs in high concentration and low concentration was conducted at the end of 2 weeks of recovery period. No significant irritation reaction such as degeneration and necrosis in vascular tissues was observed in all the histopathologic examinations.

Example 13

Effects of Compound 7, Compound 8 and DL-3-(3'-hydroxy)-butylphthalide on rat sleep Experiments for Improving Sleep Properties of the samples: the contents in the capsule formulation of Compound 7 and Compound 8 of the present invention are brown particles.

Source of animals: Kunming mice, 18~22 g, male, were clean grade animals provided by Guangdong Medical Lab Animal Center. In the breeding room of the experimental animals, the temperature was 22±2° C., the relative humidity was 55~70%, and the animal feed was provided by Guangdong Medical Lab Animal Center.

3 groups of Compound 7, Compound 8, DL-3-(3'-hydroxy)-butylphthalide (DL for short) were set in the experiment, 25 mg/kg respectively. And distilled water control group was additionally set.

Sample processing: 25 mg respective sample was taken, and added with distilled water to 20 ml, to form a uniform suspension, for use in the test.

Route for administration: gavage

Experimental Method:

Hypnosis Test of Pentobarbital Sodium in Dosage Above Threshold:

40 male mice with a body weight of 18~22 g were selected, and randomly divided into 4 groups, 10 mice in each group. They were consecutively administered with samples for 30 days, and 15 min after the administration of the samples by gavage on the 30$^{th}$ day, each group of animals were i.p. injected with 50 mg/kg.b.w pentobarbital sodium, and the injection amount was 0.2 ml/20 g.b.w. The criterion for judging falling asleep was that the righting reflex in a mouse disappeared for 1 min or more. The time for falling asleep and the sleeping time of each group of animals within 60 min were observed after administration of pentobarbital sodium.

Results:

| | | Effects of samples on the body weight of animals | | |
|---|---|---|---|---|
| | | Body weight (g) | | |
| Group | Number of animals | Beginning of the test | Interim of the test | End of the test |
| Control group | 20 | 20 ± 1.4 | 27 ± 1.6 | 35 ± 2.0 |
| Group of Compound 7 | 20 | 20 ± 1.5 | 27 ± 1.3 | 35 ± 1.6 |
| Group of Compound 8 | 20 | 20 ± 1.3 | 27 ± 1.6 | 35 ± 2.3 |
| Group of DL | 20 | 20 ± 1.2 | 27 ± 1.2 | 35 ± 2.4 |

As is shown in the above table, in comparison with the control group, the body weights of animals in each dosage group have no significant difference.

| Effects on sleeping time in mice induced by pentobarbital sodium in dosage above threshold | | | |
|---|---|---|---|
| Dosage group | Number of animals | Time for falling asleep (min) | Sleeping time (min) |
| Control group | 10 | 5.79 ± 2.05 | 40.96 ± 8.16 |
| Group of Compound 7 | 10 | 5.78 ± 1.88 | 41.16 ± 7.80 |
| Group of Compound 8 | 10 | 3.91 ± 0.99* | 53.28 ± 11.12* |
| Group of DL | 10 | 4.68 ± 1.35 | 45.48 ± 11.23 |

*$P < 0.05$, as compared to the control group (by ANOVA)

As is shown in the above table, in comparison with the control group, the time for falling asleep and the sleeping time of the animals induced by pentobarbital sodium in dosage above threshold in the group of Compound 8 ((−)-(S)-3-(3'-hydroxy)-butylphthalide) have significant difference.

Hypnosis Test of Pentobarbital Sodium in Dosage Below Threshold:

40 male mice with a body weight of 18~22 g were selected, and randomly divided into 4 groups, 10 mice in each group. They were consecutively administered with samples for 28 days, and 15 min after the administration of the samples by gavage on the 30th day, each group of animals were i.p. injected with 30 mg/kg.b.w pentobarbital sodium, and the injection amount was 0.2 ml/20 g.b.w. The criterion for judging falling asleep was that the righting reflex in a mouse disappeared for 1 min or more. The time for the occurrence of sleep of each group of animals within 25 min were observed after administration of pentobarbital sodium.

Results:

| Effects on the incidence of sleep in mice induced by pentobarbital sodium in dosage below threshold | | | |
| --- | --- | --- | --- |
| Dosage group | Number of animals | Number of animals falling asleep | Incidence of sleep (%) |
| Control group | 10 | 2 | 20 |
| Group of Compound 7 | 10 | 3 | 30 |
| Group of Compound 8 | 10 | 8* | 80* |
| Group of DL | 10 | 5 | 50 |

*P < 0.05, as compared to the control group (by chi-square test)

As is shown in the above table, in comparison with the control group, the number of animal falling asleep and the incidence of sleep in the animals induced by pentobarbital sodium in dosage below threshold in the groups of Compound 8 ((−)-(S)-3-(3'-hydroxy)-butylphthalide) and DL have significant difference.

Summary: after oral administration to mice with the samples for 30 days, the groups of Compound 8 ((−)-(S)-3-(3'-hydroxy)-butylphthalide) and DL have effects of improving sleep. The effect of the S configuration is greater than that of the racemic DL configuration, and that of the DL configuration is greater than that of the R configuration.

The invention claimed is:

1. A method of treating cerebral ischemic diseases and/or improving sleep comprising administrating an effective amount of an ester having formula II, III or IV below to a subject in need thereof:

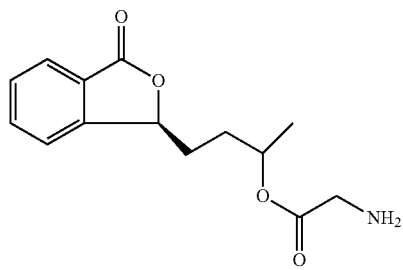

(II)

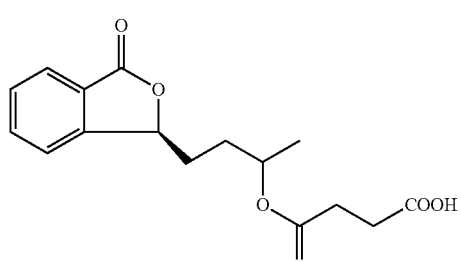

(III)

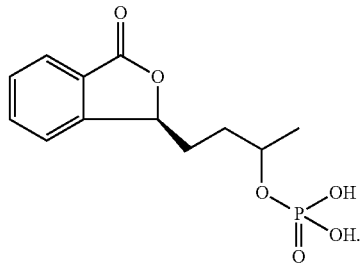

(IV)

2. A method of treating cerebral ischemic diseases and/or improving sleep comprising administrating an effective amount of an ester in the form of salt having formula V, VI or VII below to a subject in need thereof:

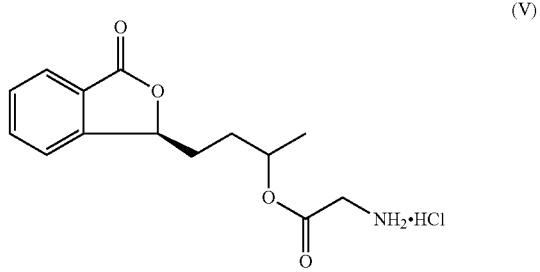

(V)

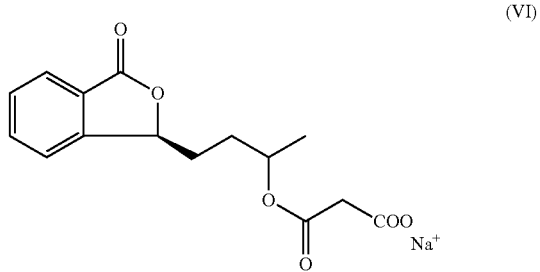

(VI)

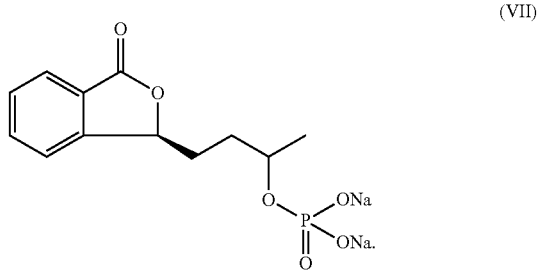

(VII)

3. A pharmaceutical composition, comprising an effective amount of an ester having formula II, III or IV below, and a pharmaceutically acceptable carrier:

19
II
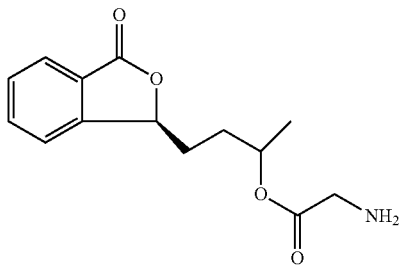
III
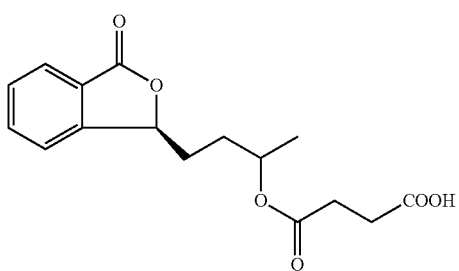
20
-continued
IV
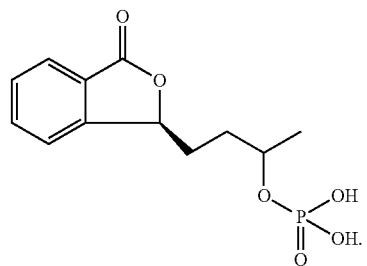
4. The pharmaceutical composition of claim 3, wherein the ester is obtained by reacting a compound of formula I with glycine, succinic acid, or phosphoric acid:
I
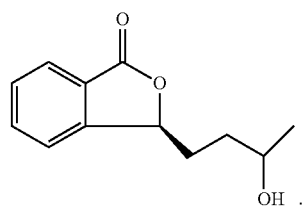
* * * * *